United States Patent [19]

Laurent

[11] Patent Number: 4,777,036

[45] Date of Patent: Oct. 11, 1988

[54] **PROCESS FOR THE CULTURE OF *BABESIA CANIS*, APPLICATION TO THE PREPARATION OF ANTIGENES AND VACCINES AND ANTIGENES AND VACCINES AGAINST PYROPLASMOSIS**

[75] Inventor: Nathalie Laurent, Marcy l'Etoile, France

[73] Assignee: Rhone Merieux, Lyons, France

[21] Appl. No.: 922,656

[22] Filed: Oct. 24, 1986

[30] Foreign Application Priority Data

Oct. 24, 1985 [FR] France ................. 85 15815

[51] Int. Cl.⁴ .............. A61K 39/018; C12N 1/10; C12Q 1/18
[52] U.S. Cl. .................... 424/88; 435/68; 435/258; 435/947
[58] Field of Search ............ 435/258, 68, 947; 424/88

[56] References Cited

U.S. PATENT DOCUMENTS

| | | | |
|---|---|---|---|
| 3,511,908 | 5/1970 | Brock et al. | 424/88 |
| 3,849,551 | 11/1974 | D'Antonio | 424/88 |
| 3,911,097 | 10/1975 | Hanson | 424/88 X |
| 4,307,191 | 12/1981 | Ristic et al. | 435/258 X |
| 4,457,915 | 7/1984 | Goodger et al. | 424/88 |
| 4,590,072 | 5/1986 | Buening et al. | 424/88 X |
| 4,596,707 | 6/1986 | Ristic et al. | 424/88 |
| 4,661,348 | 4/1987 | Wright | 424/88 |

OTHER PUBLICATIONS

Science, 193, 673–675, (1976), Trager et al.
Am. Jour. Trop. Med. Hyg., 27(5), 1061–1064, (1978), Erp et al.
Mahoney, Exp. Parasitol., 20, 232–241, (1967).

*Primary Examiner*—Howard E. Schain
*Attorney, Agent, or Firm*—Larson and Taylor

[57] ABSTRACT

In a process for the culture of *Babesia canis*, erythrocytes infected by the *Babesia canis* parasite are incubated in a culture medium suitable for the survival of the erythrocytes and for breeding of the parasites, in the presence of a homologous serum, in the substantially static state, in a normal atmosphere, first of all at a high temperature of 34° to 38° C., then a low temperature, more especially between 0° and 10° C., this cycle being able to be reproduced. The supernatant product is collected which is centrifugated and filtered. A vaccine is prepared against pyroplasmosis in dogs from this floating medium.

15 Claims, No Drawings

PROCESS FOR THE CULTURE OF *BABESIA CANIS*, APPLICATION TO THE PREPARATION OF ANTIGENES AND VACCINES AND ANTIGENES AND VACCINES AGAINST PYROPLASMOSIS

BACKGROUND OF THE INVENTION

1. Field of the Invention

The present invention relates to a method for the culture of parasites of the *Babesia canis* species. It also relates to the application of this method to the preparation of antigenes and vaccines against canine babesioses, as well as to the antigenes and vaccines obtained.

2. Description of the Prior Art

The preparation of vaccines against babesiosis has for a long time posed practically insurmountable problems. These difficulties were linked to the impossibility of breeding parasites in vitro on an industrial scale as well as to the difficulties of detecting and isolating useful antigenes, and more especially protective antigenes.

A process for breeding Babesia was proposed in Erp. et al. Am. Jour Trop. Med. Hva., 27 (5): pp. 1061–1064 (1978). This method consisted in propagating parasites in a culture of erythrocytes with mechanical stirring and with an increased carbonic gas content. This process did not however allow mass production to be reached.

The attempts made for producing babesiosis parasites using techniques close to the Plasmodium culture, described in Trager, et al., Science, 193: pp. 673–675 (1976) or Speer et al., Z. Parasitenk, 50: pp. 237–244 (1976), have not been successful.

More recently, a method has been proposed by Miodrag Ristic and Michael G. Levy, in the European patent No. 18580 for large scale production of these parasites. This method is based on incubation in erythrocytic cells in a culture medium suitable for the erythrocytes, to which is added 30 to 50% of serum, this incubation taking place statically in the presence of a controlled atmosphere containing 3 to 6% of carbonic gas and under conditions allowing the hemoglobin of the erythrocytes in the deoxidized state, to be kept at a temperature of the order of 35° to 38° C. This method has proved efficient for the large scale production of *Babesia bovis*, but not of *Babesia canis*.

It is apparent that it would be interesting to able to produce *Babesia canis* on a large scale under practical and economic conditions so as to be able to manufacture a vaccine against canine piroplasmosis.

The invention provides then such a method which allows the *Babesia canis* parasite to be produced on a large scale simply and inexpensively.

Another object of the invention is to provide such a method for preparing antigenes or vaccines from the supernatant culture products.

Another object of the invention is to provide a method for applying the culture process of the invention to the preparation of antigenes or vaccines.

A further object of the invention is to provide antigenes, purified or not, and vaccines, purified or not, from floating culture products.

The invention provides then a method for the culture of parasites of the *Babesia canis* species, in which erythrocytes infected by the parasite are incubated in a culture medium suitable for the erythrocytes, in the presence of a homologous serum, in the substantially static state, characterized in that the culture is placed in a normal atmosphere to incubate.

By normal atmosphere in the sense of the present invention is meant an atmosphere composed essentially of oxygen and nitrogen and devoid of any considerable carbonic gas content.

In a particularly advantageous embodiment of the invention, the culture is placed first of all to incubate in a high temperature, more particularly between 34° and 38° C., then at a low temperature, especially between 0° and 10° C.

Preferably, the incubation at high temperature lasts for about eight hours and at low temperature about sixteen hours. However, the incubation time at high temperature may be increased and the duration reduced during which the culture is at low temperature, this latter duration not however being preferably less than six to eight hours.

At the end of the low temperature incubation the supernatant medium is decanted and collected and is replaced by new medium, after which the culture is again placed in a high temperature to incubate, then at a lower temperature and from time to time the hematocrit is adjusted.

Advantageously, the erythrocyte concentration, i.e. the hematocrit, is of the order of 8 to 12% and preferably 10%.

Also advantageously, the culture medium comprises between 20% and 3% and preferably 5% of dog serum.

The preferred culture medium is Ham's medium F10 or F12 containing a little glucose and suitably buffered. Thus the medium may for example comprise glucose at 1g/l a Hepes buffer and bicarbonate at about 1.2%.

However other usual media may be used, such for example as 199 with Hanks salts or RPMI 1640. The culture media must be compatible with the survival of the erythrocytes and must contain the elements for breeding the parasites.

This may be obtained by starting with rich culture media and making suitable tests of them.

In the case where the culture method is intended to produce substances for administration to animals, for example a vaccine, the culture is advantageously carried out in the presence of an antibiotic such for example as gentamycine.

The culture is carried out at a suitable pH for developing the parasites, this pH being of the order of 7.3 to 7.5 and preferably of the order of 7.4.

In accordance with the invention, the suoernatant culture product is collected at the end of the low temperature incubation period. This supernatant product may be used either directly, or after purification steps, for forming antigenes and/or a vaccine against canine pyroplasmosis.

Preferably, the supernatant product is collected when the parasite concentration reaches $10^8$ parasites/ml.

Advantageously, the supernatant product is centrifugated so as to eliminate the cells, the parasites and the cell remains and parasite remains, after which sterilizing filtration is carried out. The supernatant product may then be advantageously concentrated, for example by ultra-filtration.

For preparing a vaccine, the possible contaminants of the supernatant product are then advantageously inactivated for example with formol or betapropiolactone or ethyl-ethylenimine.

The vaccine is preferably in liophilised form.

The vaccine may be administered subcutaneously.

A vaccine against piroplasmosis, in accordance with the invention, is characterized in that it contains soluble and concentrated *Babesia canis* antigenes coming from a culture supernatant of *Babesia canis* on erythrocytes. cytes.

Preferably, the dose contains at most 0.120 mg of formol and 20% of betapropiolactone or ethyl-ethylenimine.

The solvent of the liophilized vaccine comprises preferably an adjuvant and is for example in the form of a solution of saponin, for example at 0.5 mg/ml.

Other features and advantages of the invention will be clear from reading the following description, given by way of non limitative example.

EXAMPLE 1: CULTURE OF THE PARASITE

The blood is collected of a splenectomized dog infected experimentally, by intravenous injection, with a strain of *Babesia canis* congealed in liquid nitrogen. The parasitized blood is collected by intracardiac tapping, on heparine, at the final concentration of 100 U/ml. The plasma and the leucocytes are eliminated by a first centrifugation at 400 g for 10 minutes. The red globule button is then washed twice in a buffer PBS 0.15 M, pH 7.2 at 400 g for 10 minutes.

Then a suspension of the red globule button is formed at a concentration of 10% in a culture medium formed of 5% of dog serum and 95% of Ham's medium F10 containing glucose at 1g/l a Hepes buffer at 25mM, bicarbonate at 1.2% and gentamycine at 100 mg/1. The pH of the parasitized red globule suspension is adjusted to 7.4 with 1M soda.

The suspension is then divided into cellular culture bottles at the rate of 100 ml for 150 cm$^2$.

The bottles are then left to incubate in an oven in a normal humid atmosphere at a temperature of +37° C. for a period of 8 hours. Then the bottles are brought back to a temperature of +4° C. for sixteen hours.

At the end of this incubation at +4° C., the supernatant medium of the bottles is decanted and collected. This medium is replaced in the bottles by new medium and the cultures are then left again to incubate for eight hours at 37° C.

The culture cycle continues and, every 72 hours, healthy erythrocytes are added to the culture so as to readjust the hematocrit to 10% with respect to the medium.

The supernatant medium collected, freed of red globules and parasites, contains the desired antigens.

EXAMPLE 2: PREPARATION OF A VACCINE AGAINST PIROMPLASMOSIS

The supernatant media collected at the end of several successive incubations are mixed. The supernatant media mixture thus obtained is subjected to centrifugation at 700 g for eliminating the red globules and possible parasites as well as the remains thereof. The centrifugation lasts for fifteen minutes.

The medium thus centrifuged is then subjected to sterilizing filtration on a 0.22 micron membrane.

The medium is then concentrated by ultra-filtration on a membrane of 20 000 Daltons.

The concentrate is treated with formol in a proportion of 0.12 mg/ml for a night at a temperature of +4° C.

It is then lyophilized and divided into doses each corresponding to at least 10$^8$ parasites/ml.

For administration to dogs, the lyophilized vaccine is dissolved in a solution of saponin at 0.5 mg/ml in apyrogenic sterile water.

The vaccine is administered subcutaneously, preferably in the sub-scapular region, at the rate of a dose. The primary vaccination comprises two injections spaced apart by three to four weeks. Yearly or half yearly boosters are required.

The amount of saponin solvent is adapted to the weight of the dog to be vaccinated, dogs of a weight greater than 7 kilos receiving the dose dissolved in 1 ml of solvent, dogs of a weight less than 1 kilo receiving the dose dissolved in 0.5 ml of solvent.

Although the invention has been described in connection with a particular embodiment, it will of course be understood that different modifications of detail may be made thereto without for all that departing from the scope and spirit of the invention.

What is claimed is:

1. A method for the culture of parasites of the *Babesia canis* species in which erythrocytes infected by the parasite are incubated in a culture medium suitable for the survival of the erythrocytes and for breeding of the parasites, in the presence of a homologous serum, in the substantially static state, characterized in that the culture is placed in a normal atmosphere to incubate.

2. The method as claimed in claim 1, wherein the culture is placed first of all in a high temperature between 34° and 38° C., to incubate then in a low temperature between 0° and 10° C.

3. The method as claimed in claim 2, wherein the high temperature incubation lasts for about 8 hours and the low temperature incubation for about 16 hours.

4. The method as claimed in claim 1, wherein at the end of the low temperature culture, the supernatant medium is decanted, collected and replaced with new medium, after which the resulting culture is incubated at said high temperature and then at said lower temperature.

5. The method as claimed in claim 1, wherein the hematocrit is of the order of 8 to 12%.

6. The method as claimed in claim 1, wherein the culture medium comprises between 20% and 3% of dog serum.

7. The method as claimed in claim 1, wherein the medium comprises glucose at 1g/l a Hepes buffer and bicarbonate at about 1.2%.

8. The method as claimed in claim 1, characterized in that the culture is carried out at a pH of the order of 7.3 to 7.5.

9. The method as claimed in claim 1, wherein the culture is carried out in the presence gentamycine.

10. The method as claimed in claim 1, wherein the parasite inoculum is collected on heparine.

11. A method for preparing antigens and vaccines comprising collecting supernatant product from the culture product resulting from the incubation method of claim 1.

12. The application as claimed in claim 11, wherein the supernatant product is subjected to centrifugation then to sterilizing filtration.

13. The application as claimed in claim 12, wherein the sterilized supernatant product is concentrated.

14. The method as claimed in claim 11, to the preparation of a vaccine, wherein the possible contaminants of the supernatant product are inactivated and the supernatant product is lyophilized.

15. A method as claimed in claim 1 wherein the culture medium is selected from the group consisting of Ham's medium F10, F12, 199 with Hanks salts and RPMI 1640, said culture medium being buffered and containing glucose.

* * * * *